(12) United States Patent
Petit et al.

(10) Patent No.: US 10,835,299 B2
(45) Date of Patent: Nov. 17, 2020

(54) IMPLANTATION ASSEMBLY COMPRISING A DRIVE INSTRUMENT PRE-FITTED ON A BONE IMPLANT

(71) Applicant: SAFE ORTHOPAEDICS, Eragny sur Oise (FR)

(72) Inventors: Dominique Petit, Verton (FR); Constant Delahaye, Saint Ouen L'Aumone (FR); Gianluca Maestretti, Wallenried (CH); Stephane Fuentes, Marseilles (FR)

(73) Assignee: SAFE ORTHOPAEDICS, Eragny sur Oise (FR)

( * ) Notice: Subject to any disclaimer, the term of this patent is extended or adjusted under 35 U.S.C. 154(b) by 345 days.

(21) Appl. No.: 14/765,384

(22) PCT Filed: Feb. 5, 2014

(86) PCT No.: PCT/FR2014/050214
§ 371 (c)(1),
(2) Date: Aug. 3, 2015

(87) PCT Pub. No.: WO2014/122395
PCT Pub. Date: Aug. 14, 2014

(65) Prior Publication Data
US 2015/0374417 A1    Dec. 31, 2015

(30) Foreign Application Priority Data
Feb. 5, 2013   (FR) ...................................... 13 50989

(51) Int. Cl.
*A61B 17/04* (2006.01)
*A61B 17/86* (2006.01)
*A61F 2/08* (2006.01)
*A61B 17/70* (2006.01)
*A61B 17/88* (2006.01)
(Continued)

(52) U.S. Cl.
CPC ........ *A61B 17/7098* (2013.01); *A61B 17/685* (2013.01); *A61B 17/7082* (2013.01); *A61B 17/864* (2013.01); *A61B 17/8888* (2013.01); *A61B 17/3468* (2013.01); *A61B 2017/3445* (2013.01)

(58) Field of Classification Search
CPC combination set(s) only.
See application file for complete search history.

(56) References Cited

U.S. PATENT DOCUMENTS

2010/0114174 A1*   5/2010   Jones ................. A61B 17/7098
                                                              606/279
2011/0245881 A1   10/2011   Mitchell
(Continued)

FOREIGN PATENT DOCUMENTS

FR          2820630        8/2002
FR          2954689        7/2011

*Primary Examiner* — Sameh R Boles
(74) *Attorney, Agent, or Firm* — Bachman & LaPointe, P.C.

(57) ABSTRACT

The invention concerns an implantation assembly comprising a bone-anchoring element comprising a threaded rod provided at one of its ends with a head and an instrument for driving the bone-anchoring element, said instrument comprising a drive spindle removably premounted on the bone-anchoring element.

19 Claims, 6 Drawing Sheets

(51) Int. Cl.
*A61B 17/68* (2006.01)
*A61B 17/34* (2006.01)

(56) References Cited

U.S. PATENT DOCUMENTS

2011/0313471 A1   12/2011   McLean et al.
2012/0197311 A1   8/2012    Kirschman

* cited by examiner

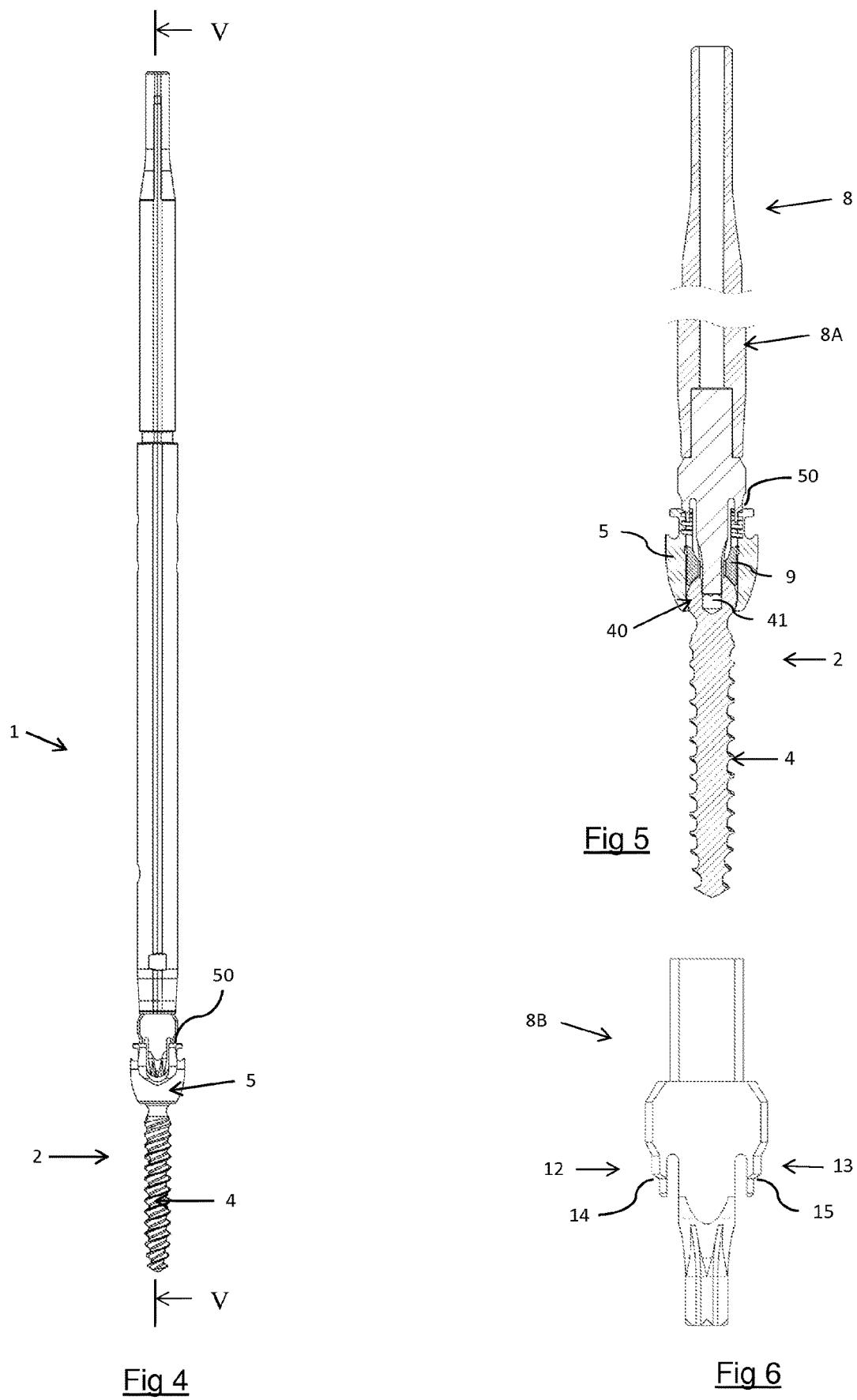

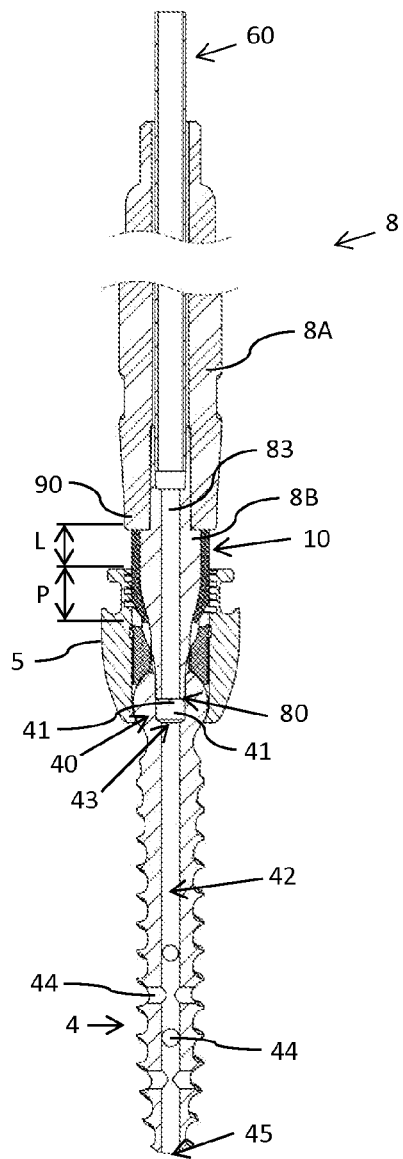
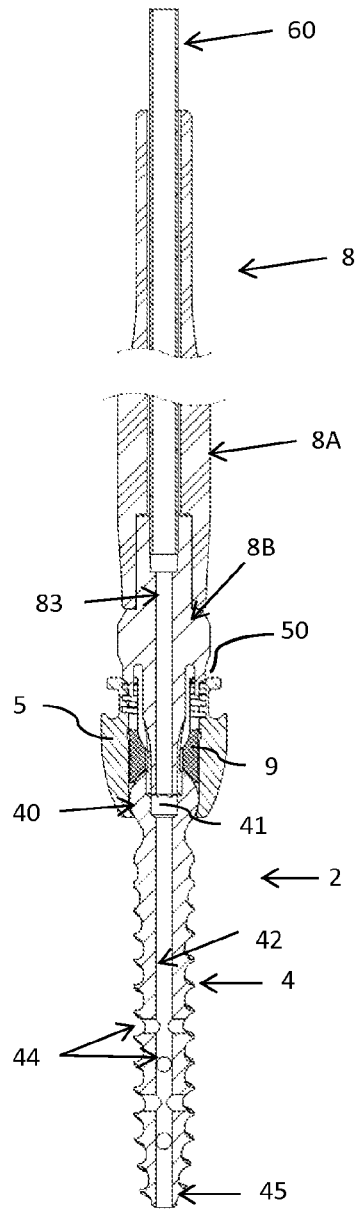
Fig 12
Fig 13

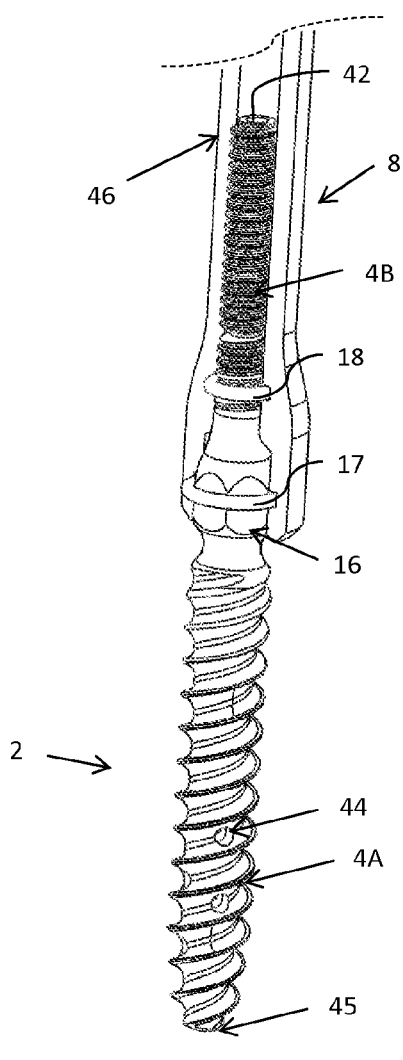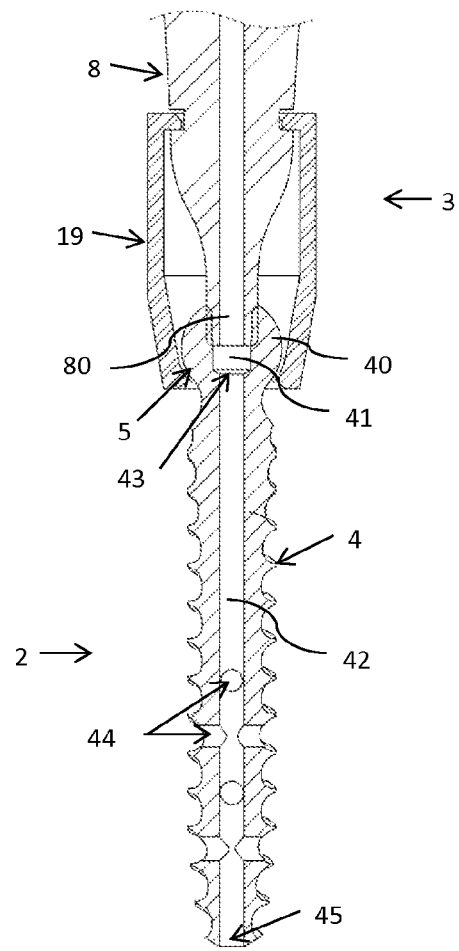
Fig 14
Fig 15

IMPLANTATION ASSEMBLY COMPRISING A DRIVE INSTRUMENT PRE-FITTED ON A BONE IMPLANT

BACKGROUND

The invention relates to the field of osteosynthesis, in particular rachidian, and more particularly that of fitting bone implants.

The invention relates more particularly to an implantation assembly comprising a bone-anchoring element and an instrument for driving the bone-anchoring element, the instrument being intended to drive the bone-anchoring element by screwing into a hole previously drilled or not in a bone structure.

By way of example, bone-anchoring elements for rachidian osteosynthesis comprise, in a known manner, a threaded rod provided at one of its ends with a head able to receive a connecting element directly or by means of a connector.

Bone-anchoring elements are intended to be fixed to the vertebrae concerned for stabilisation and/or osteosynthesis. To do this, the threaded rod of the bone-anchoring element is positioned in a hole drilled, in advance or not, in a vertebra. Once in place in the hole, the pressing of the bone-anchoring element into the vertebra is continued by means of a driving instrument, of the screwdriver type, placed on the head of the bone-anchoring element. The pressing in of the bone-anchoring element is effected until sufficient pressing in is achieved in order to ensure fixing the bone-anchoring element in the vertebra.

One of the drawbacks encountered with the driving instruments conventionally used is the wear on their end coupling with the head of the bone-anchoring element. Though this wear is related to the repeated use of the driving instruments (pairing combined with the torque exerted by the end on the bone-anchoring element), it is also linked to, or even accelerated by, recurrent sterilisation cycles after each surgical operation, during which the instruments undergo aggressive actions by solvents, decontaminants, etc. When the driving instruments are worn, the result is a loss of rigidity of the assembly consisting of driving instrument and bone-anchoring element, then increasing the risks of faulty placement of the bone-anchoring element in the vertebra.

It is moreover not rare for a surgeon to encounter difficulties in pairing the driving instrument with the bone-anchoring element. These difficulties are all the greater since the bone-anchoring element has a head able to rotate on the threaded rod (multiaxial screw). However, such difficulties in pairing may have serious consequences in terms not only of duration of a surgical operation but also operating risks. Since the surgical times are longer, it is then in general necessary to have recourse to longer periods of anaesthesia. In order to overcome these difficulties of pairing a driving instrument with a bone-anchoring element, it is common to provide a tolerance at the connection between instrument and anchoring element. The mounting of the driving element on the bone-anchoring element is then achieved to the detriment of holding the bone-anchoring element by the driving instrument. The connection between the bone-anchoring element and the driving instrument is then frequently "lost", in particular when there is a bending force on the driving instrument and therefore on the bone-anchoring element.

The invention aims to remedy these problems by proposing an implantation assembly eliminating any problem of wear on the driving instruments and any problem of pairing between such an instrument and a bone-anchoring element during a surgical operation.

Another object of the invention is to propose a functional implantation assembly for providing, at each surgical operation, surgical instruments without any wear and where sterility is guaranteed.

Another object of the invention is to propose an implantation assembly allowing optimum tolerance so as to ensure holding of the driving instrument on the bone-anchoring element, in particular when they are subjected to bending forces.

SUMMARY

To this end, and according to a first aspect, the invention relates to an implantation assembly comprising a bone-anchoring element comprising a threaded rod provided at one of its ends with a head and an instrument for driving a bone-anchoring element, said instrument comprising a drive spindle premounted removably on the bone-anchoring element.

The term "premounted" means a driving instrument the drive spindle of which is coupled so as to be secured to the bone-anchoring element, prior to the implantation of the bone-anchoring element.

Thus, because of a premounting of a single-use driving element on the bone-anchoring element, the problem of wear of the driving instrument and the problem of pairing between the two parts are avoided conjointly. Because of this, a reduction in the tolerance is allowed and rigid holding of the bone-anchoring element by the driving element is ensured when the assembly is subjected to tension forces.

Likewise, the premounting of the driving instrument on the bone-anchoring element affords firstly a saving in surgical time because of the elimination of the operation of placing the driving instrument on the bone-anchoring element and secondly by a reduction in the operating risk, the duration of anaesthesia being reduced accordingly.

Advantageously, the implantation assembly comprises means for axial holding of the drive spindle on the bone-anchoring element.

According to a particular embodiment, the implantation assembly comprises an intermediate holding part disposed between the head of the bone-anchoring element and the drive spindle of the instrument, the holding part forming the axial holding means.

Advantageously, the intermediate part comprises a tubular body having a first section complementary to a section of the head of the bone-anchoring element and a second section complementary to a section of the drive spindle. According to the configurations of the head of the bone-anchoring element and of the driving instrument, an external intermediate part may be provided, that is to say one disposed at least partially surrounding the head of the bone-anchoring element and the driving instrument, or an internal intermediate part, that is to say one disposed between the head of the bone-anchoring element and the drive spindle.

Advantageously, the intermediate holding part is formed from a flexible or elastic material. This has the advantage of allowing rotation of the drive spindle with respect to the head of the bone-anchoring element while maintaining the torque of the drive spindle with the threaded rod of the bone-anchoring element.

According to another embodiment, the drive spindle comprises two flexible lugs extending longitudinally, said lugs forming the axial holding means. Advantageously, the head is arranged with the threaded part in order to allow coupling of the drive spindle with the threaded rod of the bone-anchoring element.

Advantageously, the head is mounted on the threaded rod so as to be free to rotate with respect to the threaded rod.

According to a particular configuration, the head has a threaded longitudinal cavity emerging in a transverse channel able to receive a connecting element, the drive spindle of said instrument having an end cooperating with the bottom of the transverse channel of the head of the bone-anchoring element.

According to a particular advantageous configuration, the implantation assembly comprises at least one extension tube for the bone-anchoring element sized so as to receive the drive spindle within it, the extension tube having an end for coupling with the head of the bone-anchoring element. Advantageously, the extension tube is designed so that, when it is coupled to the head of the bone-anchoring element, it is arranged with the drive spindle so as to allow the rotation movement of the drive spindle about its longitudinal axis.

According to another advantageous configuration, said implantation assembly comprises a tissue-protection tube arranged so as to receive the bone-anchoring element within it.

Advantageously, the bone-anchoring element, on which at least one driving instrument is premounted, is disposed in a sterile sealed package.

Advantageously, the sterile package further comprises the extension tube and/or the protection tube.

Advantageously, the implantation assembly is sterile.

Advantageously, the implantation assembly is for single use.

Advantageously, the driving instrument forms a guide for a surgical instrument having a tubular body. It thus makes it possible to fix a correction instrument of the tube type once again on the bone-anchoring element.

Advantageously, the drive spindle is a screwdriver shank.

Advantageously, the implantation instrument is for single use.

According to another aspect, the invention relates to an implantation assembly comprising a bone-anchoring element and an instrument for driving the bone-anchoring element, in which the bone-anchoring element comprises a threaded rod provided at one of its ends with a head, the threaded rod comprising an axial bore having an end opening at the head and at least one radial aperture communicating with the axial bore, and the driving instrument comprising a drive spindle premounted removably on the bone-anchoring element, the drive spindle having a passage channel passing through it longitudinally, communicating with the axial bore of the bone-anchoring element.

The term "communicating" means a passage channel arranged so as to give access to the axial bore of the bone-anchoring element. It may be direct or indirect communication.

As indicated previously, the term "premounted" means a driving instrument the drive spindle of which is coupled so as to be secured to the bone-anchoring element, prior to the implantation of the bone-anchoring element.

The implantation assembly thus configured provides the distribution of a fixing substance, such as cement, or any other product, such as for example a bone treatment subject, in the bone structure in which the bone-anchoring element is implanted, eliminating any risk of leakage of the distributed substance outside the bone anchoring structure during distribution thereof.

Furthermore, this configuration allows the distribution of a substance during driving of the bone-anchoring element by the driving instrument. This has advantage of not limiting the distribution of the substance in localised areas of the bone structure corresponding to the location of the radial aperture in the threaded rod but on the contrary distributing it over a greater height. When the distributed substance is a fixing substance, the result is an improvement in fixing the bone-anchoring element in the bone structure.

The implantation assembly according to this configuration reproduces all the features of the implantation assembly previously described.

Furthermore, the threaded rod comprises a plurality of radial apertures disposed in pairs, each pair of apertures being disposed at the same distance from one another, the radial apertures in each pair being disposed so as to be diametrically opposed. According to another advantageous configuration, the threaded rod comprises a plurality of radial apertures disposed at equal distances from one another in the axial direction and equidistant from one another by 120° in the radial direction.

According to another aspect, the invention concerns a method for preparing an implantation assembly comprising an anchoring element comprising a threaded rod intended to be implanted in a bone structure and a head, the method comprising a step of mounting an extension tube on the head of the bone-anchoring element, the extension tube being guided along a drive spindle of the driving instrument premounted on the bone-anchoring element.

Once the extension tube is in place, provision can be made for removing the driving instrument from the bone-anchoring element.

BRIEF DESCRIPTION OF THE FIGURES

Other objects and advantages of the invention will emerge during the following description given with reference to the accompanying drawings, in which:

FIG. 4 depicts a schematic view of an implantation assembly according to a second embodiment of the invention;

FIG. 5 depicts a view in longitudinal section of the implantation assembly of FIG. 4 along the axis V-V;

FIG. 6 depicts a detail view of the drive spindle of the implantation assembly of FIG. 4;

FIG. 12 depicts a schematic view in cross section of an implantation assembly according to a fifth embodiment;

FIG. 13 depicts a schematic view in cross section of an implantation assembly according to a fifth embodiment;

FIG. 14 depicts a schematic view in cross section of an implantation assembly according to a fifth embodiment;

FIG. 15 depicts a schematic perspective view of an implantation assembly according to a fifth embodiment, the driving instrument being shown in cross section.

DETAILED DESCRIPTION

Figure 1:
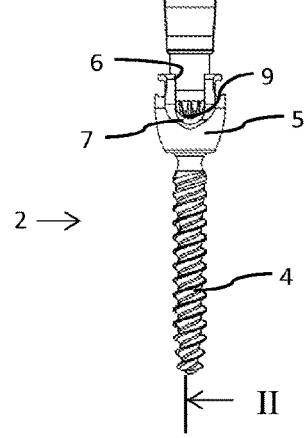
FIG. 1 depicts a schematic view of an implantation assembly comprising a driving instrument premounted on a bone-anchoring element according to a first embodiment of the invention.
Figure 2:
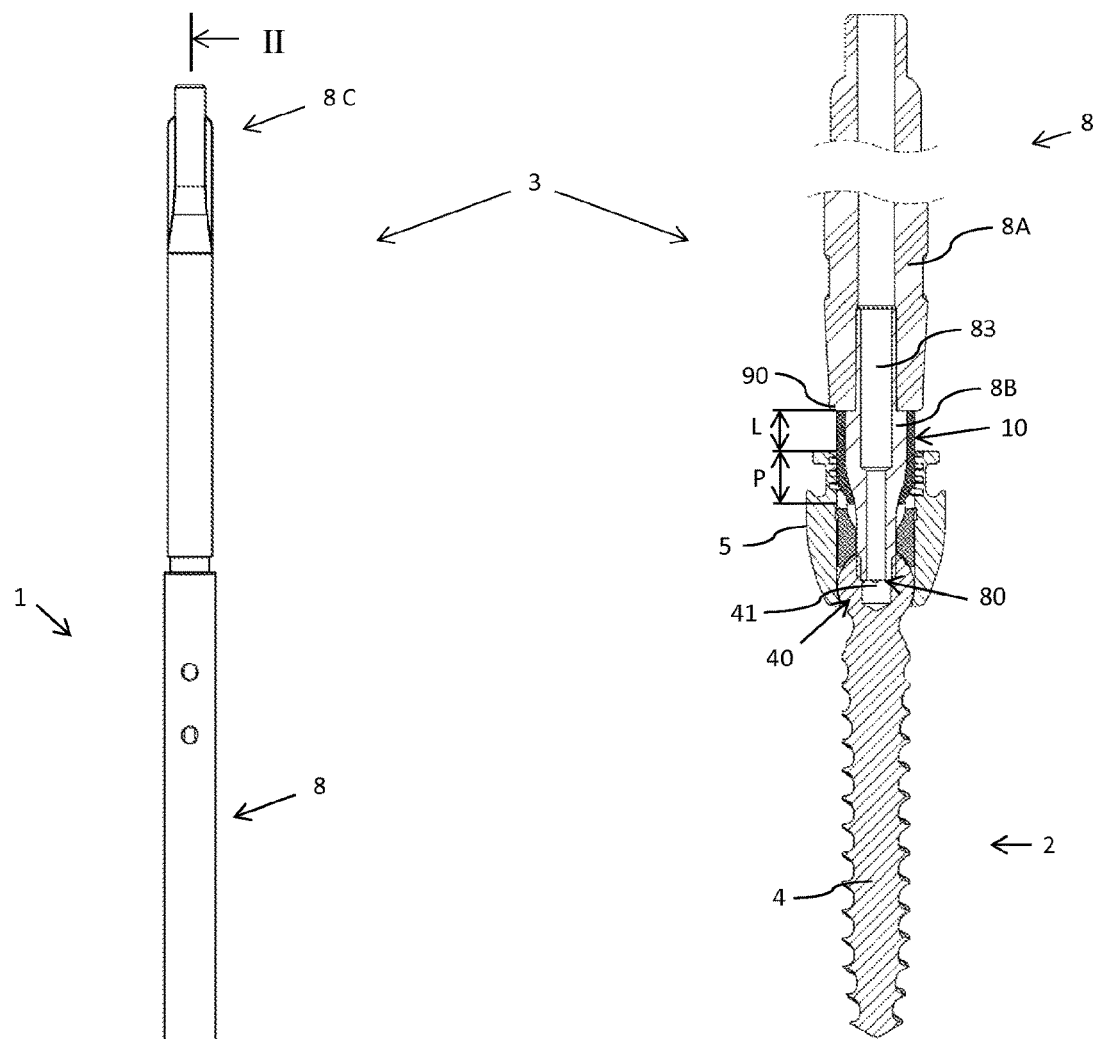
FIG. 2 depicts a view in longitudinal section of the implantation assembly of FIG. 1 along the axis II-II.
Figure 3:
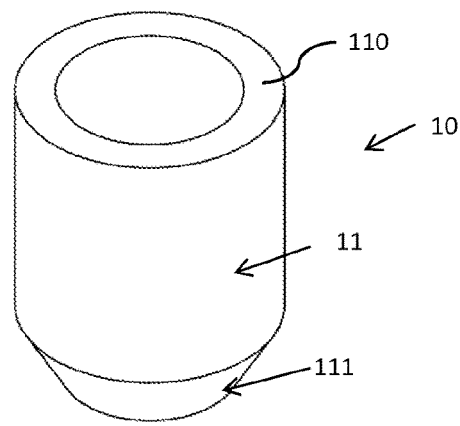
FIG. 3 depicts a schematic view of an intermediate holding part according to a particular embodiment.

In relation to FIGS. 1 to 3, a description is given of an implantation assembly 1 for osteosynthesis according to a first embodiment, said implantation assembly comprising a bone-anchoring element 2 on which an instrument 3 for driving the bone-anchoring element 2 is removably premounted.

Hereinafter, the bone-anchoring element 2 may also be designated by the term screw.

The bone-anchoring element 2 comprises a threaded rod 4 provided at one of the ends 40 thereof with a head 5 in the shape of a tulip. The head 5 thus has a threaded longitudinal cavity 6 emerging in a transverse channel 7. In a manner that is conventional per se, the transverse channel 7 is intended to receive a connecting element, for example a connecting rod, the threaded longitudinal cavity 6 being intended to receive a plug for locking the connecting element on the head 5 of the bone-anchoring element 2.

In the embodiment described, the bone-anchoring element 2 is a multiaxial screw. More particularly, the head 5 is mounted so as to be free to rotate on the threaded rod 4. To do this, the threaded rod 4 comprises a spherically shaped end 40 housed in the bottom part of the head 5, in a space provided under the transverse channel 7 and emerging in the latter. The space has an outlet opening for passage of the threaded rod 4 when the bone-anchoring element is mounted in the head 5.

Advantageously, a part forming a cradle 9 is provided at the bottom of the transverse channel 7 of the screw head 5, said part having an upper housing intended to receive the connecting element once the driving instrument 3 is removed. The part forming a cradle 9 also has a bottom face with a shape complementary to that on which it is intended to be placed. In the embodiment illustrated, the bottom face has a shape complementary to that of the end 40 of the threaded rod. The part forming a cradle 9 also comprises a through hole to allow a portion of the driving instrument 3 to pass.

In the embodiment described, the driving instrument 3 comprises a drive spindle 8 having an end 80 arranged so as to cooperate with the bottom of the transverse channel of the head 5 of the screw 2. This end 80 will be referred to hereinafter as the "connecting or coupling end 80". In the embodiment illustrated, the head 5 and the threaded rod 4 of the bone-anchoring element 2 are arranged with respect to each other so that the threaded rod 4 emerges in the transverse channel 7. The drive spindle 8 is then premounted directly on the end 40 of the threaded rod emerging in the transverse channel 7. As depicted in FIG. 2, the end 40 of the threaded rod comprises a cavity 41 with a shape complementary to the connecting end 80 of the drive spindle 8.

In the embodiment illustrated in FIG. 2, the drive spindle 8 is formed by a first part referred to as the gripping and manipulation part 8A, and a second part referred to as the connecting part 8B. The gripping part 8A is formed by a tubular elongate body in which the connecting part 8B is partially set. It is of course understood that the invention is not limited to this configuration of the driving instrument. In particular, provision may be made for the gripping and manipulation part 8A and the connecting part 8B to be formed in a single piece.

Advantageously, and as illustrated in FIG. 2, the connecting part 8B has a channel 83 passing through it longitudinally. The drive spindle 8 thus hollowed out allows, when it is in engagement with a suitable bone-anchoring element (an element with channel and windows), the injection of cement or any other product. Such an application will be described below in relation to FIG. 12.

Advantageously, as illustrated in FIG. 1, the gripping and manipulation part 8A is provided with a recess 8C for receiving a gripping handle (handle not shown). The presence of a handle has the advantage of facilitating the manipulation of the drive spindle 8.

In order to improve the holding of the drive spindle 8 on the bone-anchoring element 2, the implantation assembly 1 advantageously comprises an intermediate holding part 10 disposed between the head 5 of the bone-anchoring element 2 and the drive spindle 8 of the instrument. The intermediate holding part 10 is arranged with the head 5 and the drive spindle 8 so as to hold the latter in line with the threaded rod 4 of the bone-anchoring element 2 on which the driving instrument 3 is premounted.

According to an advantageous embodiment illustrated in FIG. 3, the intermediate holding part 10 is in the form of a tubular joint. It comprises a tubular body 11 preferably having an external cross section complementary to the internal cross section of the longitudinal cavity 6 of the screw head 5 and an internal cross section complementary to the external cross section of the drive spindle 8. More particularly, the external and internal cross sections of the holding part 10 are designed so as firstly to provide axial holding of the drive spindle 8 in the head 5 and secondly to allow a rotation movement of said spindle inside the head. Advantageously, the tubular body 11 of the intermediate holding part 10 comprises a wall 110 having a constant thickness. In the embodiment illustrated, the intermediate holding part 10 has a frustoconical end portion 111 in order to facilitate insertion thereof in the longitudinal cavity of the head 5.

It is of course understood that the form depicted in FIG. 3 is given by way of example, other forms being able to be provided so long as they ensure satisfactory axial holding of the drive spindle while allowing the rotation movement of the drive spindle about the longitudinal axis on the one hand and being able to be removed from the screw head in a relatively easy manner.

Advantageously, the intermediate holding part 10 is produced from a flexible material, such as for example an elastomer. The intermediate elastomer holding part 10 advantageously has a cross section slightly greater than the cross section of the longitudinal cavity 6 of the screw head 5. Thus, when the drive spindle 8 is mounted on the bone-anchoring element, the intermediate part 10 formed from flexible material deforms. The intermediate part thus released makes it possible to hold the drive spindle 8 coupled to the bone-anchoring element 2.

The intermediate holding part 10 is sized so as to cover at least the portion of the connecting part 8B extending in the longitudinal cavity 6 when the driving instrument 3 is premounted on the bone-anchoring element 2. In the embodiment described, the intermediate holding part 10 advantageously has a length equal to the depth P of the longitudinal cavity, to which there is added the length L of the portion of the drive spindle 8 extending between the opening of the longitudinal cavity 6 of the screw head 6 and the end 90 of the gripping part 8A. By providing such a length of the intermediate part 10, it suffices to slide the intermediate holding part 10 along the drive spindle 8 until it comes into abutment on the bottom face of the gripping part 8A in order to ensure correct positioning of the holding part on the spindle. Correct positioning means that a portion of the intermediate holding part 10 lies in the longitudinal cavity 6. The term "bottom" is given with reference to the figures. Moreover, by providing an abutment on the gripping part 8A, any sliding of the intermediate holding part 10 during premounting of the driving instrument 3 on the bone-anchoring element 2 is prevented.

Advantageously, the intermediate holding part 10 is mounted on the drive spindle 8 removably.

Apart from the implantation of the bone-anchoring element 2 in a vertebra, the drive spindle 8 constitutes a guide for surgical instruments having a tubular body. In particular, it can be used for guiding a tube itself serving as a guide for the connecting element.

According to a particular embodiment that is not illustrated, it is possible to provide an implantation assembly comprising an extension tube for the bone-anchoring element, said tube being premounted on the screw head 5 and having the drive spindle 8 pass in it. Advantageously, the extension tube has an internal cross section allowing the axial rotation movement of the drive spindle 8. Such a tube is shown not mounted in FIG. 7 (reference 30).

Figure 7:
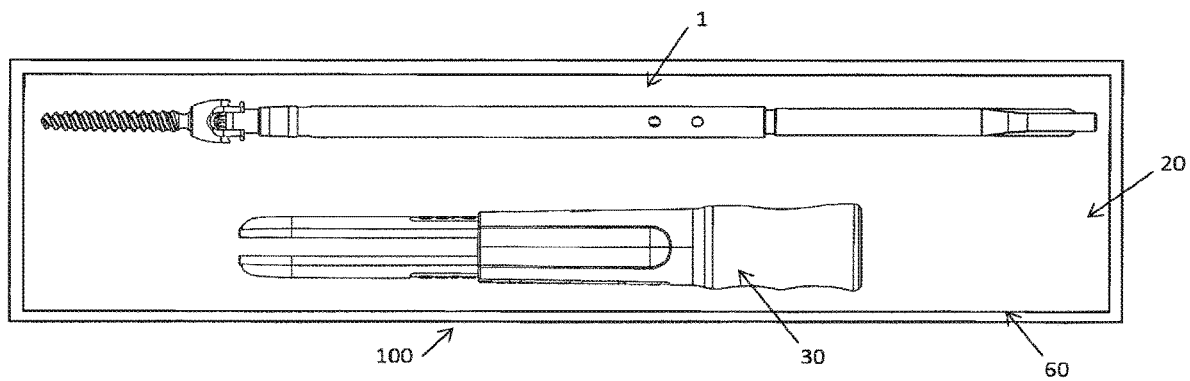
FIG. 7 depicts a view of an instrument kit comprising the implantation assembly of FIG. 1 and an extension tube.

As illustrated in FIG. 7, the premounted bone-anchoring element 2 of the driving instrument 3 is advantageously disposed in a sterile package 20. In this same package, there is also provided an extension tube 30 for the bone-anchoring element able to be mounted on the bone-anchoring element 2. Advantageously, the extension tube 30 is arranged so that, when it is coupled to the head 5 of the bone-anchoring element 2, it has the drive spindle 8 passing through it and is arranged therewith so as to allow the rotation movement of said drive spindle 8 about its longitudinal axis (the longitudinal axis of the drive spindle 8). The implantation assembly and the extension tube 30 thus disposed in a sterile package 20 form a kit 100. The kit 100 illustrated comprises an implantation assembly 1 and an extension tube 30. It is of course understood that the kit is not limited to these two instruments and that it may comprise several implantation assemblies such as several mounting tubes or any other type of single-use instrument necessary for a surgical operation. According to another variant embodiment that is not shown, provision can be made for producing a kit comprising an implantation assembly as described previously on which the extension tube is also premounted. The kit may comprise, as described previously, any type of single-use instrument necessary for a surgical operation.

Figure 8:
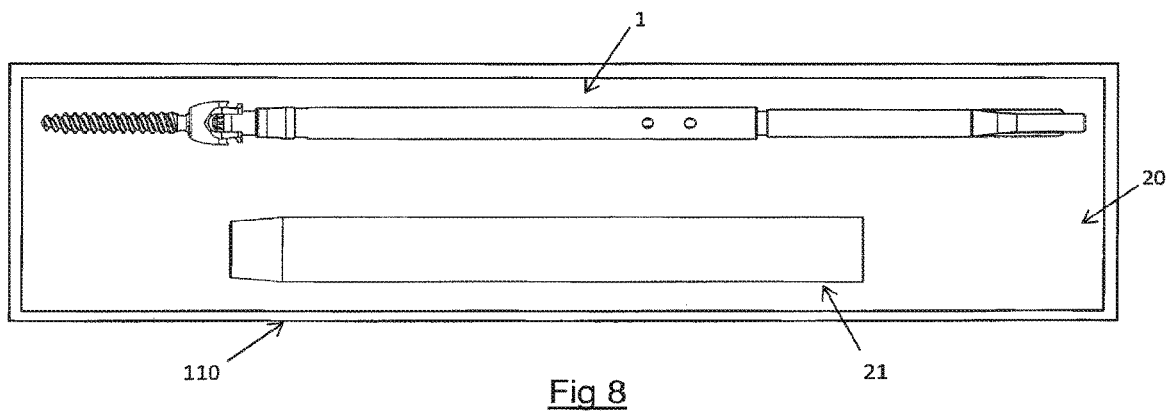
FIG. 8 illustrates a view of an instrument kit comprising the implantation assembly of FIG. 1 and a tissue protection tube.

According to a variant embodiment illustrated in FIG. 8, provision can be made for producing a kit 110 comprising an implantation assembly 1 as described previously and a tube 21 for protecting or dilating tissues or a set of protection/dilation tubes fitted in one another, and disposed in a sterile package 20. FIG. 8 illustrates an implantation assembly 1 and a protection/dilation tube or set of tubes 21 not premounted. A kit can of course be provided in which the tissue protection/dilation tube or tubes is or are premounted on the bone-anchoring element, the drive spindle passing through said tube or tubes.

FIGS. 4 to 6 illustrate an implantation assembly 1 according to another embodiment. In this embodiment, the means for holding the drive spindle 8 on the bone-anchoring element 2, formed in the previously described embodiment by the intermediate holding part 10, are provided directly on the drive spindle 8.

More particularly, the connecting part 8B comprises two elastic lugs 12, 13 extending on either side of its body in a substantially longitudinal direction. Said lugs 12, 13 are arranged so as to fit in the longitudinal cavity 6 of the drive head 5 when the driving instrument 3 is premounted on the bone-anchoring element 2. In order to ensure sufficient holding of the drive spindle 3 in the screw head 5, the connecting piece 8B has, at the spindle portion delimited by the lateral lugs 12, 13, an external cross section slightly greater than the internal cross section of the longitudinal cavity 6. Thus, when the drive spindle 8 is premounted on the head 5 of the screw 2, the elastic lugs 12, 13 are brought closer to each other to enable the spindle portion carrying the lugs to be inserted. Once released, the lugs exert a pressure on the internal surface of the longitudinal cavity 6 of the screw head 5, thus wedging the drive spindle 3 in the screw head 2.

Advantageously, the flexible lugs 12, 13 comprise respectively an external shoulder 14, 15, each shoulder being intended to come into abutment on the top face 50 of the screw head 5. The expression "external shoulder" means a shoulder extending in the direction opposite to the longitudinal cavity 6 when the driving instrument 3 is premounted on the bone-anchoring element 2. The term "top" is given with reference to the figures.

In the embodiment illustrated in FIG. 5, the connecting part 8B is shown "solid". According to an advantageous embodiment, provision may be made for the connecting part 8B to have a longitudinal channel 83, like the connecting part 8B shown in FIG. 2. The gripping and manipulation part 8A itself being tubular, this makes it possible, when the driving instrument 3 is used with a suitable bone-anchoring element (an element with channel and windows), to inject cement or other product. Such a configuration is illustrated in FIG. 13.

Figure 9:
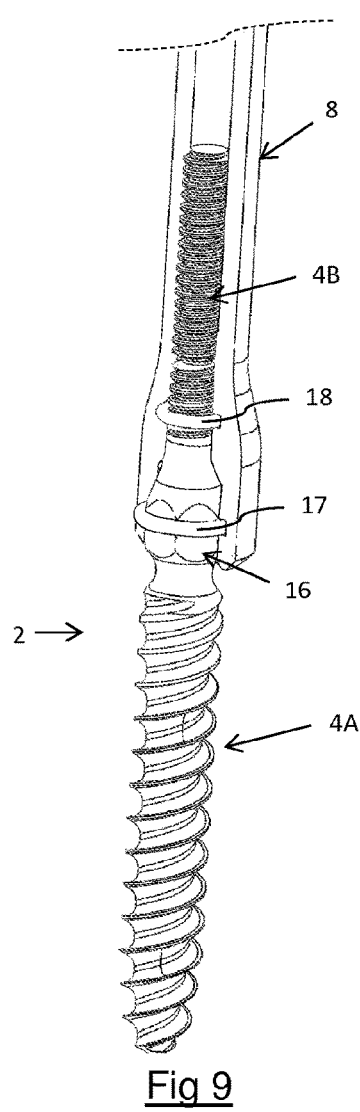
FIG. 9 depicts a schematic perspective view of an implantation assembly comprising a driving instrument premounted on a bone-anchoring element according to a third embodiment of the invention, the driving instrument being shown in cross section.
Figure 10:
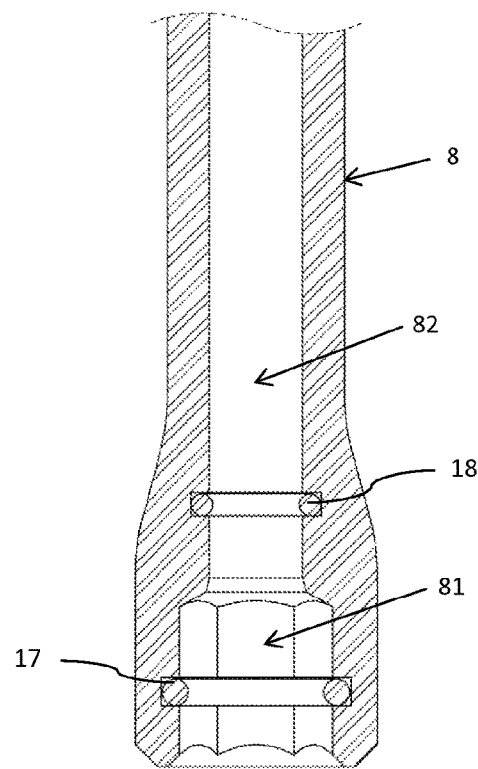
FIG. 10 depicts a detail view of the driving instrument of FIG. 9.

FIGS. 9 and 10 illustrate another embodiment of an implantation assembly. In this embodiment, the bone-anchoring element 2 comprises two threaded parts, one constituting the threaded part 4A intended to be implanted in the bone structure, the other forming a metric thread 4B. The two parts 4A, 4B extend on either side of an element 16 for driving the bone-anchoring element 4 by means of the driving instrument 3. Advantageously, the driving element 16 has a hexagonal shape. The drive spindle 8 of the driving instrument 3 for its part has a coupling end 80 provided with a reception cavity 81 with a shape complementary to that of the driving element 16. Thus, when the driving instrument 3 is mounted on the bone-anchoring element, the coupling element 80 encloses the driving element 16. The reception cavity 81 is extended axially so as to receive the metric thread 4B. The axial holding means, in the form of annular joints 17 and/or 18, advantageously produced from flexible material, are provided at the wall delimiting the reception cavity 81 and/or at the wall delimiting the extended region 82 of said cavity. Preferably, the annular joints 17 and/or 18 are elastic.

Advantageously, the extended region 82 advantageously extends over the entire length of the drive spindle 8 in order to emerge at the top end of the latter. This configuration has the advantage, when the instrument is premounted on a suitable bone-anchoring element (an element with channel and windows), of enabling cement or any other product to be injected. Such an application is illustrated in FIG. 14.

Figure 11:
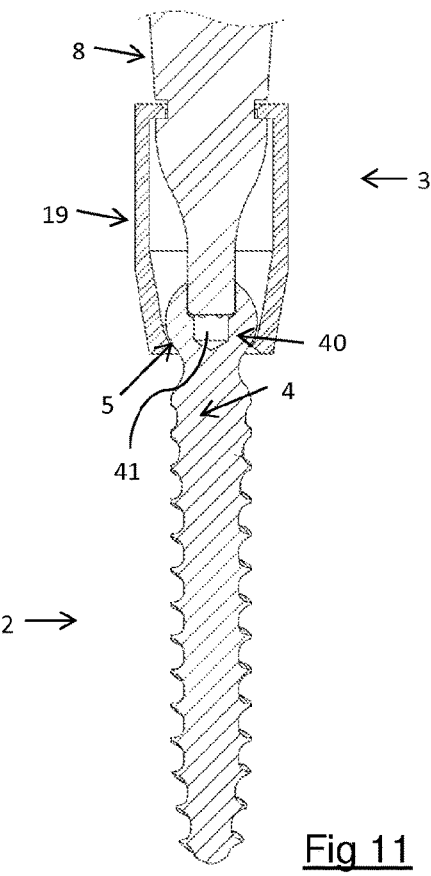
FIG. 11 depicts a schematic detail view of an implantation assembly comprising a driving instrument premounted on a bone-anchoring element according to a fourth embodiment of the invention.

FIG. 11 illustrates another embodiment of an implantation assembly. In this embodiment, the head 5 of the bone-anchoring element 2 is formed by the spherical end 40 of the threaded rod 4. As before, the head comprises a longitudinal cavity 41 for receiving the coupling end 80 of the driving instrument 3. In this embodiment, the holding means comprise an external part in the form of a collar 19 for holding the driving instrument 3 on the head 5 when mounted on the head 5. According to the form of the head and of the driving instrument, a holding collar having a non-constant internal cross section may be provided.

In this embodiment, the drive spindle is shown "solid". According to an advantageous embodiment, provision may be made for this to have a channel to enable it to be used with a suitable bone-anchoring element (element with channel and windows) for the purpose of injecting cement or any other product, as illustrated in FIG. 15.

FIGS. 12 to 15 illustrate the implantation assemblies previously described, configured to allow the injection of substances, such as fixing substances for improving the fixing of the bone-anchoring element in the bone structure (cement), treatment substances, or any other substance able to be injected. The implantation assemblies repeat all the features previously described in relation to FIGS. 1 to 11.

In addition to these features, the bone-anchoring element 2 comprises an axial bore 42 extending from the end opposite to the anchoring end 45 (spherical end 40 for the embodiments illustrated in FIGS. 12, 13, 15; end 46 of the threaded part 4B for the embodiment illustrated in FIG. 14). It further comprises radial apertures 44 communicating with the axial bore 42 (only six are shown). In the embodiment described, the axial bore 42 has an end opening 43 at the end 40 of the threaded rod emerging in the cavity 41. The axial bore on the other hand does not have an opening at the end opposite to the end 40 in the axial direction. In the examples illustrated, the bone-anchoring element comprises eight radial apertures (only six being shown). It is of course understood that the number of radial apertures may vary without departing from the scope of the invention.

According to a particular configuration, the radial apertures 44 are disposed in pairs. The radial apertures in each pair are disposed so as to be diametrically opposed, while each pair is disposed at a given distance from the others. Advantageously, the pairs of apertures are disposed at equal distances from one another. According to another configuration that is not shown, the apertures are disposed at equal distances from one another in the axial direction and equidistant from one another by 120° in the radial direction. It is of course understood that the invention is not limited to these configurations, the number and location of the apertures being able to vary without departing from the scope of the invention.

Moreover, and as indicated previously, the driving instrument has a channel. More particularly, the drive spindle 8 is arranged to have a passage channel extending over the entire length of said spindle 8. The channel is arranged so as to communicate, directly or indirectly, in the axial bore of the bone-anchoring element. Direct communication means a passage channel emerging directly in the axial bore of the bone-anchoring element (FIG. 14); indirect communication means a passage channel communicating with the axial bore of the bone-anchoring element by means of a cavity: in FIGS. 12, 13 and 15, the connecting end 80 is not fitted in as far as the bottom of the cavity 41 provided at the spherical end 40 of the bone-anchoring element. Because of this, the passage channel emerges in a portion of the cavity 41 which itself communicates with the axial bore 42.

Advantageously, the injection of cement or other substance is carried out by means of a cannula 60 inserted in the passage channel of the drive spindle. FIGS. 12 and 13 show a partial view of the cannula 60 mounted in the channel. It is of course obvious that this is a particular embodiment for injecting substances. Use of a cannula is in fact not essential since the cement and other substances can be injected directly into the passage channel.

As in the embodiments previously described, the implantation assemblies illustrated in FIGS. 12 to 15 are advantageously disposed in a sterile package 20. In this same package, it will also be possible to provide one or more extension tubes for the bone-anchoring element able to be mounted on the bone-anchoring element, one or more tissue protection or dilation tubes or any other type of single-use instrument necessary for a surgical operation so as to form a kit.

The invention is described above by way of example. Naturally a person skilled in the art is in a position to implement different variant embodiments of the invention without departing from the scope of the invention.

The invention claimed is:

1. An implantation assembly comprising:
    a bone-anchoring element comprising a threaded rod provided with a head at one end of said bone-anchoring element, the threaded rod comprising an axial bore having an end opening at the head and at least one radial aperture communicating with the axial bore,
    said bone-anchoring element being integrally provided with a removable injection spindle having a passage channel passing through the injection spindle longitudinally, and an end arranged to cooperate with the end opening of the threaded rod so that said passage channel of the injection spindle communicates directly with the axial bore of the bone-anchoring element for injecting substances with said injection spindle being a drive shaft of a screwdriver for driving the bone-anchoring element, said bone-anchoring element provided with the injection spindle is disposed in a sterile sealed packaging.

2. The implantation assembly according to claim 1, further comprising means for axial holding of the drive spindle on the bone-anchoring element.

3. The implantation assembly according to claim 2, further comprising an intermediate holding part disposed between the head of the bone-anchoring element and the drive spindle of the instrument, the holding part forming the axial holding means.

4. The implantation assembly according to claim 3, wherein the intermediate part comprises a tubular body having a first cross section complementary to a cross section of the head of the bone-anchoring element and a second cross section complementary to a cross section of the drive spindle.

5. The implantation assembly according to claim 4, wherein the intermediate holding part is formed from a flexible material.

6. The implantation assembly according to claim 2, wherein the drive spindle comprises two flexible lugs extending longitudinally, said lugs forming the axial holding means.

7. The implantation assembly according to claim 1, wherein the head has a threaded longitudinal cavity emerging in a transverse channel able to receive a connecting element, the drive spindle of said instrument having an end cooperating with the bottom of the transverse channel of the head of the bone-anchoring element.

8. The implantation assembly according to claim 1, wherein the head is arranged with the threaded part configured to couple the drive spindle with the threaded rod of the bone-anchoring element.

9. The implantation assembly according to claim 1, wherein the head is mounted on the threaded rod so as to be free to rotate with respect to the threaded rod.

10. The implantation assembly according to claim 1, wherein said assembly comprises at least one tube extending the bone-anchoring element, said tube sized to receive within it the drive spindle, the extension tube having an end for coupling with the head of the bone-anchoring element.

11. The implantation assembly according to claim 1, wherein said assembly comprises a tissue-protection tube configured to receive the bone-anchoring element within said tube.

12. The implantation assembly according to claim 1, wherein the sterile package also comprises at least one of an extension tube and/or the tissue-protection tube.

13. The implantation assembly according to claim 1, wherein said assembly is sterile.

14. The implantation assembly according to claim 1, wherein said assembly is for single use.

15. The implantation assembly according to claim 1, wherein the driving instrument is configured to form a guide for a surgical instrument having a tubular body.

16. The implantation assembly according to claim 1, wherein the threaded rod comprises a plurality of radial apertures disposed in pairs, each pair of apertures being disposed at the same distance from one another, the radial apertures in each pair being disposed so as to be diametrically opposed.

17. The implantation assembly according to claim 1, wherein the threaded rod comprises a plurality of radial apertures disposed at equal distances from one another in the axial direction and equidistant from one another by 120° in the radial direction.

18. The implantation assembly according to claim 1, wherein said assembly comprises a cannula for injecting substances disposed in the passage channel of the drive spindle.

19. The implantation assembly according to claim 1, wherein the implantation instrument is for single use.

* * * * *